United States Patent
Kadhiresan et al.

(10) Patent No.: US 7,269,458 B2
(45) Date of Patent: Sep. 11, 2007

(54) CARDIOPULMONARY FUNCTIONAL STATUS ASSESSMENT VIA HEART RATE RESPONSE DETECTION BY IMPLANTABLE CARDIAC DEVICE

(75) Inventors: Veerichetty Kadhiresan, Centerville, MN (US); Donald Hopper, Maple Grove, MN (US); Richard Fogoros, Pittsburg, PA (US); Lemont Baker, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 174 days.

(21) Appl. No.: 10/914,632

(22) Filed: Aug. 9, 2004

(65) Prior Publication Data
US 2006/0030892 A1 Feb. 9, 2006

(51) Int. Cl.
A61N 1/00 (2006.01)
A61B 5/04 (2006.01)

(52) U.S. Cl. ............... 607/19; 607/17; 607/18; 607/9; 600/509; 600/519; 600/513

(58) Field of Classification Search ............... 607/9, 607/17, 18, 19; 600/509, 513, 519
See application file for complete search history.

(56) References Cited

U.S. PATENT DOCUMENTS

| | | | |
|---|---|---|---|
| 6,161,042 A | 12/2000 | Hartley et al. | |
| 6,190,324 B1 * | 2/2001 | Kieval et al. | 600/483 |
| 6,273,856 B1 | 8/2001 | Sun et al. | |
| 6,459,929 B1 | 10/2002 | Hopper et al. | |
| 6,519,495 B1 | 2/2003 | Sun et al. | |
| 6,529,771 B1 | 3/2003 | Kieval et al. | |
| 6,539,249 B1 | 3/2003 | Kadhiresan et al. | |
| 6,572,557 B2 | 6/2003 | Tchou et al. | |
| 6,645,153 B2 * | 11/2003 | Kroll et al. | 600/481 |
| 6,741,885 B1 | 5/2004 | Park et al. | |
| 6,752,765 B1 | 6/2004 | Jensen et al. | |
| 7,016,730 B2 * | 3/2006 | Ternes | 607/17 |
| 7,031,766 B1 * | 4/2006 | Paris | 600/519 |
| 7,171,271 B2 * | 1/2007 | Koh et al. | 607/19 |
| 2002/0151936 A1 | 10/2002 | Kloss et al. | |
| 2003/0060854 A1 | 3/2003 | Zhu | |
| 2004/0127944 A1 | 7/2004 | Casset | |
| 2006/0036290 A1 | 2/2006 | Hooper et al. | |

\* cited by examiner

*Primary Examiner*—Carl Layno
*Assistant Examiner*—Natasha Patel
(74) *Attorney, Agent, or Firm*—Schwegman, Lundberg, Woessner & Kluth, P.A.

(57) ABSTRACT

An implantable cardiac device is configured and programmed to assess a patient's cardiopulmonary function by evaluating the patient's heart rate response. Such evaluation may be performed by computing a heart rate response slope, defined as the ratio of an incremental change in intrinsic heart rate to an incremental change in measured activity level. The heart rate response slope may then be compared with a normal range to assess the patient's functional status.

18 Claims, 2 Drawing Sheets

CARDIOPULMONARY FUNCTIONAL STATUS ASSESSMENT VIA HEART RATE RESPONSE DETECTION BY IMPLANTABLE CARDIAC DEVICE

FIELD OF THE INVENTION

This present disclosure pertains to cardiac rhythm management devices such as pacemakers and implantable cardioverter/defibrillators.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers have been used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate and/or artificially restoring AV conduction. Pacing therapy may also be used to treat ventricular conduction disorders by pacing both ventricles in order to result in a more coordinated contraction, termed cardiac resynchronization therapy.

In pacemaker patients who are chronotropically incompetent (e.g., sinus node dysfunction), the heart rate is determined solely by the pacemaker in the absence of intrinsic cardiac activity. That heart rate is determined by the programmed escape intervals of the pacemaker which cause paces to be delivered to the atria and/or ventricles, depending upon the pacing mode, if no intrinsic beats occur before expiration of the escape intervals. Pacing the heart at a fixed rate as determined by the length of the programmed escape intervals, however, does not allow the heart rate to increase with increased metabolic demand. It is for this reason that rate-adaptive pacemakers have been developed which vary the programmed escape intervals in accordance with one or more physiological parameters related to metabolic demand such as obtained from an accelerometer or minute ventilation sensor. In chronotropically competent patients in need of ventricular pacing, on the other hand, atrial triggered pacing modes such as DDD or VDD are desirable because they allow the pacing to track the physiologically normal atrial rhythm, which causes cardiac output to be responsive to the metabolic needs of the body. For this latter group of patients, the pacemaker is normally programmed so that the atrial rate is overridden by an atrial or ventricular pace only if the atrial rate drops to a level considered unsafe.

In a chronotropically competent patient with cardiac disease, the change in heart rate in response to exercise is a useful indicator of the patient's cardiopulmonary functional status. A decrease in cardiopulmonary function, for example, often manifests as an increased heart rate for a given workload since the heart must beat faster to produce the needed cardiac output. An improvement in cardiopulmonary function, on the other hand, may be indicated by a decreased heart rate with the same workload. Evaluation of cardiopulmonary function in this manner is normally performed by exercise testing in a formal clinical setting. The present disclosure relates to a way of assessing a patient's cardiopulmonary function by utilizing the sensing capabilities of an implantable cardiac device.

DETAILED DESCRIPTION

Figure 1:
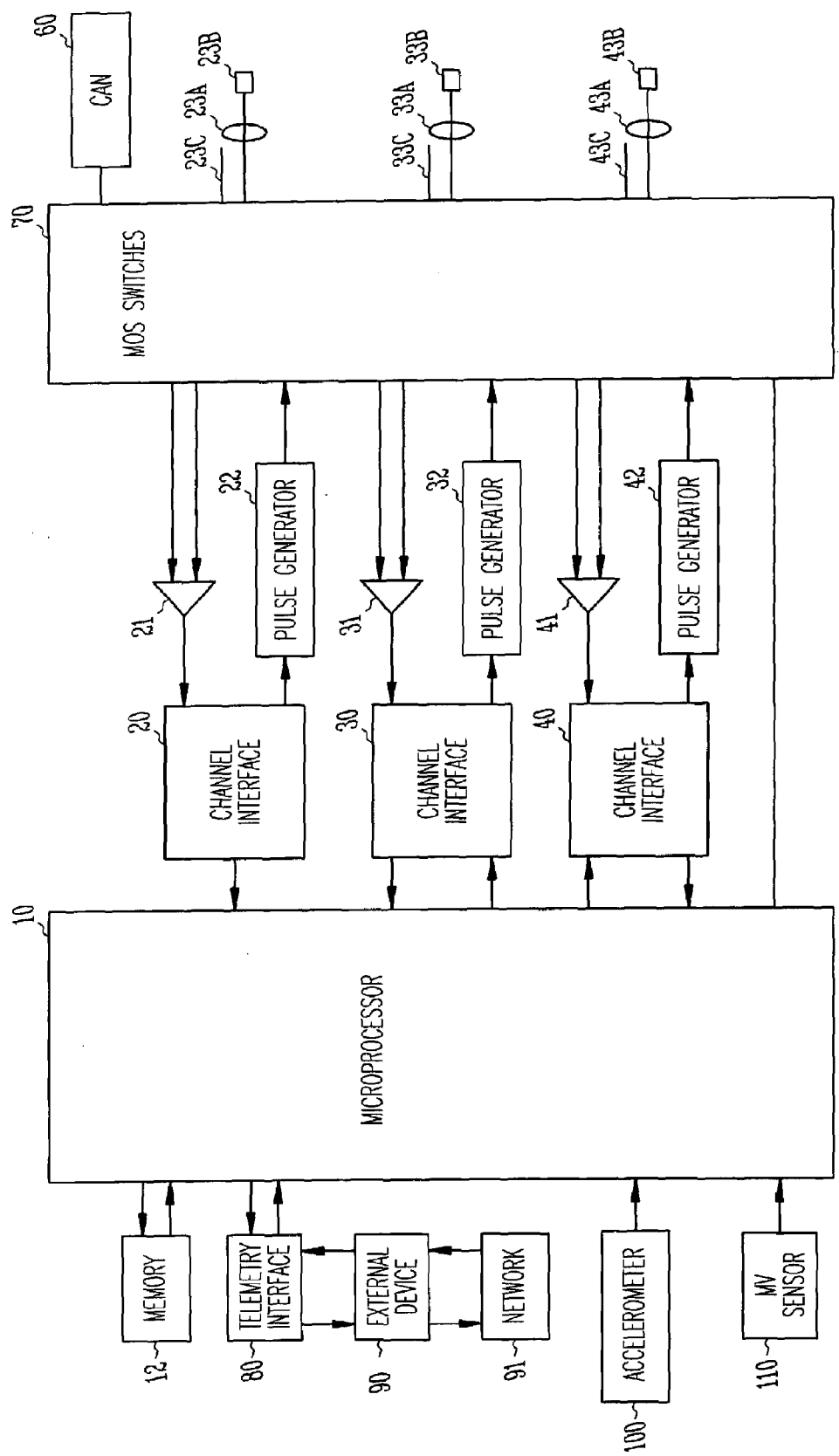
FIG. 1 is a block diagram of an exemplary cardiac rhythm management device.

Many patients implanted with a cardiac rhythm management device (e.g., a conventional pacemaker, resynchronization pacemaker, defibrillator, combination device, or heart monitor) exhibit an appropriate adjustment in heart rate (HR) in response to exercise. That is, these patients are chronotropically competent so that the atrial rate as determined by the sino-atrial node responds appropriately to the increased metabolic demand brought about by increased physical activity. The reason for which they are implanted with the device may be, for example, to restore AV conduction, to treat ventricular conduction delays with resynchronization therapy, and/or to deliver anti-tachycardia pacing or defibrillation shocks in the event of an arrhythmia. In these patients, the implanted device may be configured to allow the patient's own physiology to determine heart rate either by not delivering pacing therapy at all, delivering pacing therapy only as a safety measure, or delivering pacing therapy in an atrial triggered mode. This affords an implanted device with appropriate sensing capabilities the opportunity to assess a patient's cardiopulmonary functional status by monitoring the patient's heart rate response to physical activity. As noted above, cardiac rhythm management devices may be equipped with an accelerometer to measure physical activity levels for use in rate-adaptive pacing modes. Unlike minute ventilation, the physical activity level as measured by an accelerometer is an indication of the actual work performed by a patient which is not dependent upon the patient's individual physiology. The present disclosure relates to a cardiac device equipped with an activity level sensor which is programmed to collect measurements of heart rate and activity level over some period of time in order to monitor cardiopulmonary function.

In one embodiment, the device constructs a historical record of activity level versus heart rate, referred to as a heart rate response profile. The heart rate response profile may be stored in the device's memory and later downloaded for use by a clinician in evaluating the cardiopulmonary functional status of the patient and determining if any trend is present. The device may also be programmed to evaluate the patient's heart rate response by computing one or more heart rate response parameters, either on a continuous basis, at periodic intervals, when triggered by particular detected events, or when commanded to do so via telemetry. The device may then compare the computed heart rate response parameter to a normal range in order to assess the patient's cardiopulmonary status in real-time. If the device determines that the heart rate response is out of the normal range and that some type of intervention may be warranted, an alarm flag is set. (An alarm flag is any type of internal indication of the out of range condition which is stored in the device's memory.) The device may then transmit the relevant information via a telemetry link to clinical personnel, either when interrogated by an external programmer or immediately over a patient management network as described below.

As aforesaid, in order to evaluate a patient's heart rate response, one or more heart rate response parameters may be derived from the heart rate and activity level measurements. One example of a heart rate response parameter is the heart rate recovery time, defined as the time required for the heart rate to recover to its normal resting rate when the activity level quickly decreases from some degree of activity to the resting level. Another example of a heart rate response parameter is the heart rate response slope, defined as the ratio of an incremental change in heart rate corresponding to an incremental change in activity level. Heart rate response slopes may be derived from the heart rate response profile for a plurality of different activity level ranges. In order to assess cardiopulmonary function, the heart rate response parameter(s) may be compared with normal ranges defined by upper and lower limit values. The range of the heart rate response parameter which is considered normal may be pre-specified, either in accordance with the average values in a representative population or as specifically derived for an individual patient, or may be computed from heart rate and accelerometer data collected by the device over some period of time. For example, an increase in a heart rate response slope above some limit may indicate that the patient is worsening and should be treated with additional device therapy and/or drug therapy in order to improve the slope. A decrease in the heart rate response slope, on the other hand, may indicate improved cardiac function. If a decrease in the heart rate response slope occurs concomitantly with a decrease in the patient's maximum intrinsic heart rate, however, there is the possibility that the patient is becoming chronotropically incompetent. The device may be programmed to compute a maximum intrinsic heart rate parameter for evaluating this possibility by collecting maximum heart rates over some period of time (e.g., daily, weekly, or monthly maximum heart rates). The maximum heart rates may be stored, for example, in the form of a histogram which is then used to compute and update a parameter which is reflective of the maximum intrinsic heart rate that the patient is able to attain.

In another embodiment, posture data is collected by a posture sensor along with the heart rate and activity data. Knowledge of posture may further improve the specificity of the heart rate slope by accounting for the postural position of the person is (e.g. sitting vs. standing). Corrections can then be made to account for postural influences on heart response to a sensed activity. Further, postural dynamics data which is trended and stored simultaneously with activity and heart rate can provide some additional indications as to patient functional status.

In another embodiment, the device may be programmed to automatically adjust its operating parameters based upon the functional status assessment in order provide more appropriate treatment to the patient. For example, if the patient's cardiopulmonary status has worsened to some predetermined extent as indicated by an increase in the heart rate response slope, the device may be programmed to initiate cardiac resynchronization therapy and/or adjust resynchronization parameters such as the AV delay or biventricular offset interval. The device may also use the heart rate response slope in conjunction with the maximum intrinsic heart rate parameter to monitor chronotropic status. If the maximum intrinsic heart rate parameter has decreased below some predetermined limit (or is decreasing at a particular rate) and the heart rate response slope has decreased so some predetermined extent, the device may be programmed to assume that the patient has become chronotropically incompetent and initiate a rate-adaptive pacing mode.

1. Exemplary Implantable Device Description

Assessment of cardiopulmonary function as described above may be implemented in any type of cardiac device (e.g., a conventional pacemaker, resynchronization pacemaker, defibrillator, combination device, or heart monitor) having the necessary sensing capabilities for measuring heart rate and activity level. Described below is an implantable cardiac rhythm management device which may be programmed to collect the needed data and perform a cardiopulmonary function assessment.

Cardiac rhythm management devices are contained within a housing which is usually implanted subcutaneously on the patient's chest and connected to electrodes by leads threaded through the vessels of the upper venous system into the heart. An electrode can be incorporated into a sensing channel that generates an electrogram signal representing cardiac electrical activity at the electrode site and/or incorporated into a pacing or shocking channel for delivering pacing or shock pulses to the site. A block diagram of an exemplary implantable cardiac rhythm management device is shown in FIG. 1. The controller of the device is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to executable code stored in memory or other storage medium. The controller is capable of operating the device so as to deliver a number of different therapies in response to detected cardiac activity. A telemetry interface 80 is also provided for enabling the controller to communicate with an external device 90 via a wireless telemetry link. The external device 90 may be an external programmer which can be used to program the implantable device as well as receive data from it or a remote monitoring unit. The external device 90 may also be interfaced to a patient management network 91 enabling the implantable device to transmit data and alarm messages to clinical personnel over the network. The network connection between the external device 90 and the patient management network 91 may be implemented by, for example, an internet connection, over a phone line, or via a cellular wireless link.

The embodiment shown in FIG. 1 has three sensing/pacing channels, where a pacing channel is made up of a pulse generator connected to an electrode while a sensing channel is made up of the sense amplifier connected to an electrode. A MOS switch matrix 70 controlled by the microprocessor is used to switch the electrodes from the input of a sense amplifier to the output of a pulse generator. The switch matrix 70 also allows the sensing and pacing channels to be configured by the controller with different combinations of the available electrodes. A sensing/pacing channel may include ring electrode 43a (33a or 23a) and tip electrode 43b (33b or 23b) of bipolar lead 43c (33c or 23c), sense amplifier 41 (31 or 21), pulse generator 42 (32 or 22), and a channel interface 40 (30 or 20). The channels may be configured as either atrial or ventricular channels. For example, the device may be configured for atrial pacing and either single ventricle or biventricular (resynchronization) pacing. The channel interfaces communicate bi-directionally with a port of microprocessor 10 and may include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. A shock pulse generator (not shown) may also be interfaced to the controller for delivering defibrillation shocks between an electrode and the housing or can 60 as selected by the switch matrix. In the illustrated embodiment, the device is equipped with bipolar leads that include two electrodes which are used for outputting a pacing pulse and/or sensing intrinsic activity. Other embodiments may employ unipolar leads with single electrodes for sensing and pacing which are referenced to the device housing or can 60 (or another electrode) by the switch matrix 70.

The controller 10 controls the overall operation of the device in accordance with programmed instructions stored in memory and with information derived from the sensing channels. The voltages sensed by the sensing electrodes are electrogram signals that are analogous to a surface ECG and provide a temporal record of cardiac depolarization and repolarization that occurs during either intrinsic or paced beats. The sensing circuitry of the pacemaker generates chamber sense signals (i.e., atrial or ventricular senses) when voltages sensed by the electrodes of a particular channel exceed a specified threshold. The controller 10 interprets sense signals from the sensing channels in order to detect arrhythmias and to control the delivery of paces in accordance with a pacing algorithm that employs such senses to trigger or inhibit pacing. Most pacing modes are so-called demand modes where a heart chamber is paced upon expiration of an escape interval without receipt of a sense from that chamber. For example, in an atrial triggered mode, an atrial sense initiates an AV escape interval so that one or both ventricles are then paced upon expiration of the interval if no intrinsic ventricular activity occurs beforehand. The ventricles may also be paced upon expiration of an escape interval initiated by a ventricular sense or pace, and the atria may be paced by a ventriculo-atrial escape interval initiated by a ventricular sense or pace.

Also interfaced to the controller are a minute ventilation sensor 110 and an accelerometer 100 for use in measuring a parameter related to the patient's exertion level and adjusting the pacing rate of the device accordingly in rate-adaptive pacing modes. The accelerometer and minute ventilation sensor produce a signal which approximates the patient's exertion level by measuring body activity and respiratory volume rate, respectively. The minute ventilation sensor measures the respiratory volume by injecting bursts of excitation current between excitation electrodes and measuring a transthoracic voltage drop to derive a signal proportional to the transthoracic impedance. (A particular minute ventilation sensor is described in U.S. Pat. No. 6,161,042, assigned to the assignee of the present application and hereby incorporated by reference in its entirety.) In a rate-adaptive pacing mode, one or more escape intervals are adjusted in accordance with a measured exertion level so that the pacing rate varies with metabolic demand. The modified pacing rate dictated by a rate-adaptive algorithm is referred to as the sensor-indicated rate. The rate-adaptive algorithm calculates the sensor-indicated rate by mapping a measured exertion level to a heart rate in accordance with a function referred to as the response factor.

A posture sensor may also be interfaced to the controller for determining the patient's posture when the heart rate and activity level is measured. In one embodiment, the accelerometer 100 is a multi-axis accelerometer which allows the controller to compute the patient's posture from measured accelerations along the multiple axes.

2. Exemplary Implementation

Figure 2:
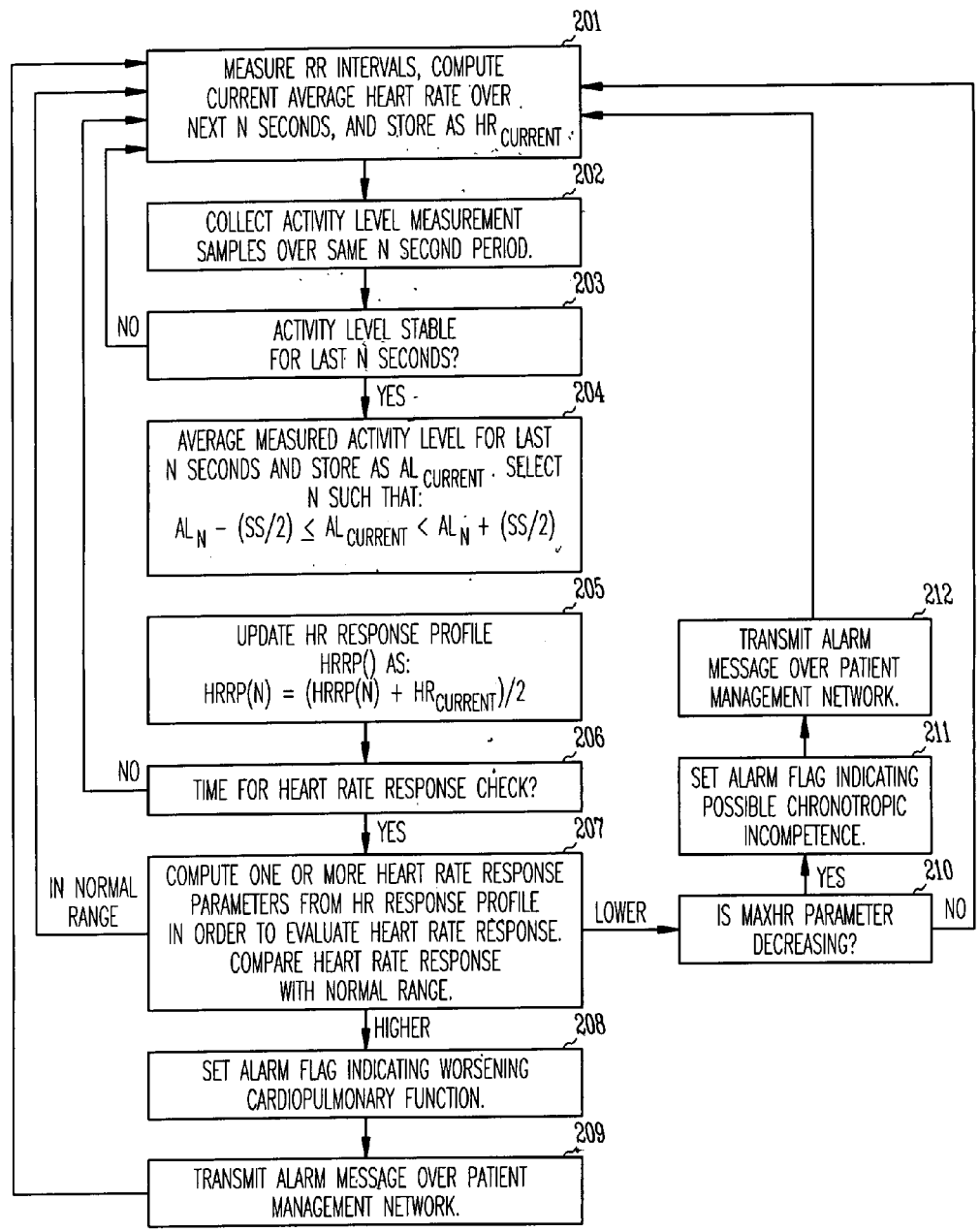
FIG. 2 illustrates an exemplary algorithm for monitoring cardiopulmonary functional status.

There are many ways in which an implantable device may implement and use the technique for assessing cardiopulmonary function as described above. Illustrated in FIG. 2 is one particular exemplary algorithm for assessing cardiopulmonary function which could be implemented in an implantable cardiac rhythm management device by appropriate programming of the device controller. In an alternative embodiment, part of the processing burden in executing the algorithm may be assumed by an external programmer in communication with the device. The device is programmed to collect measured activity levels and corresponding intrinsic heart rates in order to construct a heart rate response profile which reflects how the patient's heart rate varies with activity level. In this example, the heart rate response profile is a data structure HRRP( ) containing a plurality of heart rates indexed by an integer n, where n=0 to K. Each integer n corresponds to one of K discrete activity levels $AL_n$, where n=0 corresponds to no activity and n=K corresponds to the maximum activity level. Each activity level $AL_n$ is separated by a specified step size SS such that:

$AL_{n+1}=AL_n+SS$ for $n=0$ to $K-1$

The heart rate response profile HRRP is constructed and updated by measuring a current heart rate, measuring a current activity level to determine an integer n such that the current activity level is close to $AL_n$, and then updating the entry for HRRP(n) with the current heart rate.

Starting at step 201, RR or AA intervals (i.e., the intervals between successive ventricular or atrial senses) are measured and used to compute an average heart rate over the next N seconds. The average intrinsic heart rate thus computed is stored as $HR_{current}$. Simultaneously with the collection of RR intervals and computation of the intrinsic heart rate, the device collects corresponding activity level measurements over the same N second period at step 202, where the activity level measurements are samples of the accelerometer output taken at some sampling interval. At step 203, the device determines whether or not the collected activity level measurements meet some predefined stability criterion. For example, a variance or similar statistic of the measurements could be computed and compared with a limit value. If the activity level is judged as not sufficiently stable, the device returns to step 201 to collect RR intervals and activity level measurements for the next N second interval. In addition to requiring that the activity level is stable, a postural criterion may also be imposed at step 203 so that the device returns to step unless the patient is in a particular posture. If the activity level is judged to have been stable for the last N seconds at step 203 (and the optional postural criterion is met), the average of the activity level measurement samples over the last N seconds is stored as $AL_{current}$ at step 204, and an integer n is selected such that:

$AL_n-(SS/2) \leq AL_{current} < AL_n+(SS/2)$

At step 205, the heart rate response profile HRRP( ) is updated as:

$HRRP(n)=(HRRP(n)+HR_{current})/2$

At step 206, the device determines whether it is time to check the patient's heart rate response, as determined by either a command input or expiration of a specified time interval. If so, the device evaluates the patient's heart rate response at step 207 by computing one or more heart rate response parameters (such as a heart rate response slope) from the heart rate response profile and comparing the parameter(s) with normal ranges. If the heart rate response is within the normal range, the device returns to step 201. If the heart rate response is above the normal range, an alarm flag indicating a worsening cardiopulmonary function is set at step 208, an alarm message is transmitted over the patient management network at step 209, and the device returns to step 201. If the heart rate response is below the normal range, the device checks the maximum intrinsic heart rate parameter MaxHR at step 210. If the MaxHR parameter is not decreasing, an improving functional status is assumed and the device returns to step 201. If the MaxHR parameter is decreasing, there is the possibility of chronotropic incompetence. An alarm flag indicating such is set at step 211, an alarm message is transmitted over the patient management network at step 212, and the device then returns to step 201. The device may also be programmed to automatically initiate a rate-adaptive pacing mode if the decrease in heart rate response and maximum intrinsic heart rate are severe enough to warrant such automatic intervention. In that case, the device may be further programmed to calculate a response factor for rate-adaptive pacing based upon previously measured heart rates and exertion levels.

In a modification to the implementation described above, postural data is collected and included in the heart rate response profile. Each heart rate HRRP(n) in the profile has an associated posture indication PI(n). Analysis of the slope of the heart rate response or other parameters may then be performed in a manner which takes the patient's posture into account.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A cardiac device, comprising:
   one or more sensing channels for generating intra-cardiac electrogram signals;
   a controller for detecting intrinsic cardiac activity and measuring an intrinsic heart rate from the electrogram signals;
   an activity level sensor interfaced to the controller for measuring a parameter related to a patient's level of physical activity;
   wherein the controller is programmed to construct a historical record of activity level versus heart rate, referred to as a heart rate response profile;
   wherein the controller is programmed to compute a heart rate response slope from the heart rate response profile, defined as the ratio of an incremental change in intrinsic rate to an incremental change in measured activity level;
   wherein the controller is programmed to collect periodic maximum heart rates over time and derive a maximum intrinsic heart rate parameter therefrom indicative of the maximum heart rate the patient is able to attain;
   a pacing channel for pacing a cardiac chamber, wherein the controller is programmed to control the delivery of pacing pulses in accordance with a programmed mode; and,
   wherein the controller is programmed to switch to a rate-adaptive pacing mode if both the heart rate response slope and maximum intrinsic heart rate parameters have decreased below respective predefined limit values.

2. The device of claim 1 wherein the heart rate response profile is a data structure containing a plurality of heart rates, each heart rate being associated with a discrete activity level.

3. The device of claim 2 wherein the controller is programmed to update the heart rate response profile by averaging a currently measured heart rate with the heart rate associated with an activity level corresponding to a currently measured activity level.

4. The device of claim 2 wherein the controller is programmed to update the heart rate response profile by averaging a currently measured heart rate with the heart rate associated with an activity level corresponding to a currently measured activity level if activity level measurements taken over an N second interval meet a predefined stability criterion.

5. The device of claim 1 wherein the controller is programmed to set an alarm flag if the heart rate response slope is not within a normal range as defined by upper and lower limit values.

6. The device of claim 5 further comprising:
   a telemetry interface for communicating with a remote monitoring device; and,
   wherein the controller is programmed to send an alert message via the telemetry interface if an alarm flag is set.

7. The device of claim 1 wherein the controller is further programmed to calculate a response factor for rate-adaptive pacing based upon previously measured heart rates and activity levels.

8. The device of claim 1 wherein the controller is further programmed to compute a heart rate response parameter and to set an alarm flag if the heart rate response parameter is not within a normal range as defined by upper and lower limit values.

9. The device of claim 1 further comprising a posture sensor and wherein the controller is programmed to include postural data in the heart rate response profile.

10. A method for operating a cardiac device, comprising:
    generating intra-cardiac electrogram signals and measuring an intrinsic heart rate from the electrogram signals;
    measuring a parameter related to a patient's level of physical activity; constructing a historical record of activity level versus heart rate, referred to as a heart rate response profile
    monitoring a patient's cardiopulmonary functional status by computing a heart rate response slope from the heart rate response profile, defined as the ratio of an incremental change in intrinsic rate to an incremental change in measured activity level;
    collecting periodic maximum heart rates over time and deriving a maximum intrinsic heart rate parameter from the collected periodic maximum heart rates that reflects the maximum intrinsic heart rate that the patient is able to attain over a defined period of time;
    pacing a cardiac chamber in accordance with a programmed mode; and,
    switching to a rate-adaptive pacing mode if both the heart rate response slope and maximum intrinsic heart rate parameters have decreased below respective predefined limit values.

11. The method of claim 10 wherein the heart rate response profile is a data structure containing a plurality of heart rates, each heart rate being associated with a discrete activity level.

12. The method of claim 11 further comprising updating the heart rate response profile by averaging a currently measured heart rate with the heart rate associated with an activity level corresponding to a currently measured activity level.

13. The method of claim 11 further comprising updating the heart rate response profile by averaging a currently measured heart rate with the heart rate associated with an activity level corresponding to a currently measured activity level if activity level measurements taken over an N second interval meet a predefined stability criterion.

14. The method of claim 10 further comprising setting an alarm flag if the heart rate response slope is not within a normal range as defined by upper and lower limit values.

15. The method of claim 14 further comprising send an alert message via a telemetry interface if an alarm flag is set.

16. The method of claim 10 further comprising calculating a response factor for rate-adaptive pacing based upon previously measured heart rates and activity levels.

17. The method of claim 10 further comprising computing a heart rate response parameter and setting an alarm flag if the heart rate response parameter is not within a normal range as defined by upper and lower limit values.

18. The method of claim 10 further comprising collecting postural data and wherein the heart rate response profile includes the postural data.

* * * * *

UNITED STATES PATENT AND TRADEMARK OFFICE
CERTIFICATE OF CORRECTION

PATENT NO. : 7,269,458 B2  
APPLICATION NO. : 10/914632  
DATED : September 11, 2007  
INVENTOR(S) : Kadhiresan et al.

Page 1 of 1

It is certified that error appears in the above-identified patent and that said Letters Patent is hereby corrected as shown below:

On The Title Page, Item (56), under "U.S. Patent Documents", line 17, delete "Hooper et al." and insert --Hopper et al.--, therefor.

Signed and Sealed this

First Day of January, 2008

JON W. DUDAS  
*Director of the United States Patent and Trademark Office*